United States Patent
Lamott

(10) Patent No.: US 9,943,813 B2
(45) Date of Patent: Apr. 17, 2018

(54) DYNAMIC MIXER AND USE THEREOF

(71) Applicant: Muhlbauer Technology GmbH, Hamburg (DE)

(72) Inventor: Karsten Lamott, Hamburg (DE)

(73) Assignee: Muhlbauer Technology GmbH, Hamburg (DE)

( * ) Notice: Subject to any disclaimer, the term of this patent is extended or adjusted under 35 U.S.C. 154(b) by 0 days.

(21) Appl. No.: 15/038,170

(22) PCT Filed: Dec. 4, 2014

(86) PCT No.: PCT/EP2014/076582
§ 371 (c)(1),
(2) Date: May 20, 2016

(87) PCT Pub. No.: WO2015/082620
PCT Pub. Date: Jun. 11, 2015

(65) Prior Publication Data
US 2016/0288066 A1    Oct. 6, 2016

(30) Foreign Application Priority Data

Dec. 4, 2013  (DE) .................... 20 2013 009 790 U

(51) Int. Cl.
*B01F 7/00*    (2006.01)
*A61C 5/68*    (2017.01)
(Continued)

(52) U.S. Cl.
CPC ............ *B01F 7/00291* (2013.01); *A61C 5/68* (2017.02); *A61C 9/0026* (2013.01);
(Continued)

(58) Field of Classification Search
CPC  B01F 7/00216; B01F 7/00766; B01F 13/002; B01F 7/00641; B01F 2215/0039;
(Continued)

(56) References Cited

U.S. PATENT DOCUMENTS

| 4,851,571 A | 7/1989 | Sauer et al. |
| 6,394,643 B1 * | 5/2002 | Bublewitz ............ A61C 9/0026 |
| | | 222/145.6 |

(Continued)

FOREIGN PATENT DOCUMENTS

| CA | 2698840 | 10/2015 |
| DE | 3611048 | 10/1987 |

(Continued)

OTHER PUBLICATIONS

International Search Report and Written Opinion for PCT/EP20124/076582, dated Mar. 23, 2015, 11 pages.
(Continued)

*Primary Examiner* — Charles E Cooley
(74) *Attorney, Agent, or Firm* — Casimir Jones, S.C.; Mary Ann D. Brow

(57) ABSTRACT

A dynamic mixer, useful for mixing components of viscous compounds, in particular for components of dental impression compounds, and use thereof, the mixer having a mixing tube that contains a drivable rotor and that has on one end an end wall having at least two inlet openings for components, and at the other end an outlet opening for the mixture thereof. The rotor has a rotor disk having at least one entraining element that faces the end wall, and at least one rotor disk opening for the components to pass through to the side of the rotor disk that is remote from the end wall. At least one mixing element is arranged on the rotor hub between the rotor disk and the outlet opening. At least one projecting pin is arranged on the end wall toward the rotor disk, and the at least one entraining element has at least one recess for the at least one pin.

14 Claims, 4 Drawing Sheets

(51) Int. Cl.
*B01F 13/00* (2006.01)
*A61C 9/00* (2006.01)
*B05C 17/005* (2006.01)

(52) U.S. Cl.
CPC ...... *B01F 7/00216* (2013.01); *B01F 7/00275* (2013.01); *B01F 7/00641* (2013.01); *B01F 7/00766* (2013.01); *B01F 13/002* (2013.01); *B01F 2215/0027* (2013.01); *B01F 2215/0039* (2013.01); *B05C 17/00566* (2013.01)

(58) Field of Classification Search
CPC ......... B01F 2215/0027; B01F 7/00275; B01F 7/0025–7/00333; A61C 9/0026; A61C 5/68; B05C 17/00566
USPC ......... 366/172.2, 176.1, 181.5, 325.1, 325.2, 366/326.1, 329.1, 329.2; 222/145.5, 222/145.6
See application file for complete search history.

(56) References Cited

U.S. PATENT DOCUMENTS

| | | | |
|---|---|---|---|
| 6,540,395 B2 | 4/2003 | Muhlbauer et al. | |
| 6,837,399 B1* | 1/2005 | Wagner | A61C 9/0026 222/1 |
| 6,837,612 B2* | 1/2005 | Bublewitz | A61C 9/0026 222/145.6 |
| 6,932,243 B2* | 8/2005 | Keller | B01F 7/00141 222/145.6 |
| 9,522,366 B2* | 12/2016 | Linne | A61C 9/0026 |
| 9,656,224 B2* | 5/2017 | Linne | B01F 7/00233 |
| 2013/0329517 A1* | 12/2013 | Linne | A61C 9/0026 366/290 |
| 2013/0336083 A1* | 12/2013 | Linne | A61C 9/0026 366/279 |
| 2016/0288066 A1* | 10/2016 | Lamott | A61C 9/0026 |

FOREIGN PATENT DOCUMENTS

| | | |
|---|---|---|
| DE | 102004020410 | 12/2005 |
| EP | 0291819 | 11/1988 |
| EP | 1110599 | 6/2001 |
| WO | 2009/033832 | 3/2009 |
| WO | 2012/1166883 | 9/2012 |

OTHER PUBLICATIONS

International Preliminary Report on Patentability for PCT/EP20124/076582, dated Jun. 16, 2016, 10 pages (English Translation).

* cited by examiner

DYNAMIC MIXER AND USE THEREOF

CROSS REFERENCE TO RELATED APPLICATION

The present application is a § 371 US National Entry of International Application No. PCT/EP2014/076582, filed Dec. 4, 2014, which claims the benefit of German Application No. 202013009790.6, filed Dec. 4, 2013.

FIELD OF THE INVENTION

The invention relates to a dynamic mixer for viscous compounds, in particular for components of dental impression compounds, and to the use thereof for dental impression compounds.

BACKGROUND OF THE INVENTION

EP 0 492 412 B discloses connecting to a device for discharging the components to be mixed a dynamic mixer that has an outlet opening for the mixture at its one end. It includes a mixing tube, a rotor that is mounted and drivable rotatably therein and that, with the mixing tube, delimits a mixing duct that is annular in cross section, and an end wall having inlet openings through which the components to be mixed reach the mixing duct. The rotor has mixing impellers that are intended to blend with one another the components flowing through the mixing duct.

In this context, it is also known to provide one of the inlet openings, through which, in the event of typically dissimilar ratios of the individual components to be mixed, a relatively large quantity of the one component is to pass, with a larger cross section than the inlet openings through which a relatively small quantity of the other components is to pass. This is disclosed in EP 1 110 599 A1, inter alia.

The components of dental impression compounds have different flow behaviors. In order to guarantee the determined impression quality and the determined processing and hardening times, a blend that is as uniform, fast and homogeneous as possible must be ensured. Here, the increase in temperature and the ejection pressure must be kept as low as possible.

SUMMARY OF THE INVENTION

The object of the invention is to provide a dynamic mixer that is an improvement on the prior art.

This object is achieved by a dynamic mixer according to the main claim. Advantageous further developments form the subject matter of the dependent claims.

Accordingly, the invention relates to a dynamic mixer for the components of viscous compounds, in particular for the components of dental impression compounds, having a mixing tube and, arranged therein, a drivable rotor, wherein the mixing tube has at its first end an end wall having at least two inlet openings for the components, and at its other end an outlet opening for the mixture, wherein the rotor has a rotor disk having at least one entraining element that faces the end wall, and at least one rotor disk opening for the components to pass through to the side of the rotor disk remote from the end wall, wherein at least one mixing element is arranged on the rotor hub between the rotor disk and the outlet opening of the mixing tube, and wherein at least one projecting pin is arranged on the end wall toward the rotor disk, and the at least one entraining element has at least one recess for the at least one pin.

At its first end, the mixing tube may be connected to a container having discharge openings and a discharge device for the components. Because of the at least one entraining element, in the mixer according to the invention the components that enter through the inlet openings initially follow the rotation of the rotor.

This entrainment has the effect that the first component, which has entered through a first inlet opening, is guided past the inlet opening for a further component. During this, the first component is blended with the component that enters through the further inlet opening, as a result of which at this point in time a mixture of the individual components that is still very heterogeneous is present. As the components are fed further to the mixer, the region between the end wall and the rotor disk is substantially initially entirely filled up before the described mixture is then pressed through the at least one rotor disk opening in the rotor disk. In the region between the rotor disk and the outlet opening of the mixing tube, the mixture is further homogenized by the at least one mixing element before it is output at the outlet opening.

The invention is based on the realization that the homogeneous blending of the individual components can be improved, even over a broad range of viscosities, if the typically prevailing different flow behaviors of the individual components to be mixed is compensated to the greatest possible extent at the start of the mixing procedure. This compensation is achieved by the interaction of the according to the invention at least one pin, facing the rotor disk, on the end wall and the at least one entraining element in the region of the at least one recess. Because the at least one entraining element has a recess through which the said at least one pin slides when the rotor rotates, the compound that is upstream of the entraining element, as seen in the direction of rotation, is subjected to shear force. As a result, the viscosity thereof can be reduced and thus the miscibility with further components can be improved. The mixture that is produced in this way then passes through the at least one rotor disk opening and reaches the at least one mixing element and is further mixed there. The homogenized mixture is then output from the outlet opening of the mixer.

As a result of the arrangement according to the invention of at least one pin on the end wall, the homogeneity of the mixture that is output from the outlet opening of the mixer can be markedly improved by comparison with a mixer without such pins. At the same time, the temperature of the components and the mixture is not substantially increased.

The improvement in the miscibility can be explained by way of an example: in a dental impression compound, it is necessary to blend together for example a base paste and a catalyst paste in a predetermined ratio—for example 5:1. Here, the said pastes flow through inlet openings of different sizes (5:1) and into a dynamic mixer. If a mixer according to the invention is used, a quantity of base paste that is entrained by an entraining element as the rotor rotates can in this case be subjected to shear force by the at least one pin that is provided according to the invention before this quantity of base paste is guided past the inlet opening for the catalyst paste. As a result, the viscosity of the base paste is reduced and consequently the miscibility with the catalyst paste is improved.

It is preferable if the at least one pin has a length that is at least ⅔ of the spacing from the end wall to the rotor disk. Further preferably, the at least one pin extends as far as the rotor disk. Particularly preferably, the height of the at least one entraining element of the rotor disk and the length of the at least one pin are substantially the same.

Preferably, the spacing between the end wall and the rotor disk is substantially at least 5%, preferably at least 10%, further preferably 10 to 30% of the total length of the mixing tube.

It is preferable if more than one pin is provided on the end wall. As a result of a plurality of pins, the viscosity of a compound can be reduced to a greater extent and/or differences in viscosity in the components can be better compensated than by a single pin. In this context, the pins or at least groups of pins can be arranged in each case at the same spacing from the axis of the rotor. This provides the advantage that all the pins or at least the pins in one group can be guided through the same recess.

It is preferable if the at least one pin is arranged, as seen in the direction of rotation of the rotor, between a first, larger and a second, smaller inlet opening. As a result of an arrangement of this kind, the viscosity of the component that enters through the first inlet opening is reduced before this component has the second or further components added to it. If the mixer is used for dental impression compounds, the first, larger inlet opening is preferably provided for the base paste and the second, smaller inlet opening is preferably provided for the catalyst paste.

The end of the at least one entraining element that is remote from the axis of the rotor is preferably curved in the direction of rotation. The said end of the at least one entraining element is thus constructed in the form of a bucket, with the result that, in the region of the end that is constructed in the form of a bucket, the compound that is upstream of an entraining element, as seen in the direction of rotation of the rotor, is urged in the direction of the axis of the rotor.

The at least one rotor disk opening, for the pre-mixed components to pass through to the side of the rotor disk remote from the end wall, is preferably a radial slot. On the side of the rotor disk remote from the end wall, at least one arm that is substantially flush with a slot is further preferably arranged on the rotor hub. The component mixture that passes through the rotor disk opening is deflected by the arm and subjected to shear force. It is preferable if the number of arms corresponds to the number of rotor disk opening.

It is preferable if the at least one mixing element takes the form of a mixing impeller that projects from the rotor hub and extends as far as the inner wall of the mixing tube. Here, the front edge of the mixing impeller, as seen in the direction of rotation of the rotor, preferably runs parallel to the rear edge. Preferably, more than one mixing element is provided. The mixing elements are in that case preferably arranged in a plurality of mixing element groups that are spaced in the axial direction of the axis of the rotor, wherein the mixing elements of a mixing element group are arranged in a plane perpendicular to the axis of the rotor.

A deflecting element can be provided in a mixing element group. The deflecting element can in this case be arranged between the front edge of a first mixing element and the rear edge of the adjacent mixing element and make the free surface between the two mixing elements smaller. As a result, the mixture that strikes against the deflecting element, parallel to the axis of the rotor, flows more pronouncedly in the direction of the adjacent mixing element. As an alternative, a deflecting element can also be constructed in a manner detached from the mixing elements, that is to say take a shape that is independent of mixing elements. Preferably, the mixing element group that is closest to the outlet opening of the mixing tube does not include a deflecting element.

The mixer according to the invention is preferably used for dental impression compounds of all types (0-3). For an explanation of this use, the reader is referred to the statements made above. In this case, the dental impression compound preferably has a base paste and a catalyst paste.

The mixer according to the invention performs in particular thorough mixing both of highly viscous pastes (for example elastomeric impression materials of type 0, ISO 4823) at relatively low dynamic pressures and also of low-viscosity pastes (for example elastomeric impression materials of type 3, ISO 4823). Furthermore, the mixing of highly shear-thinning and thixotropic components is also improved. The mixer is consequently universally usable, that is to say that it is usable over a broad range of very different materials. As a result, a user can use one mixer for all the materials required in day-to-day practice, as a result of which the potential source of errors in selecting the correct mixer is eliminated.

BRIEF DESCRIPTION OF THE DRAWINGS

The invention will now be described by way of example, using an advantageous embodiment and with reference to the attached drawings, in which.

DESCRIPTION OF THE INVENTION

Figure 1:
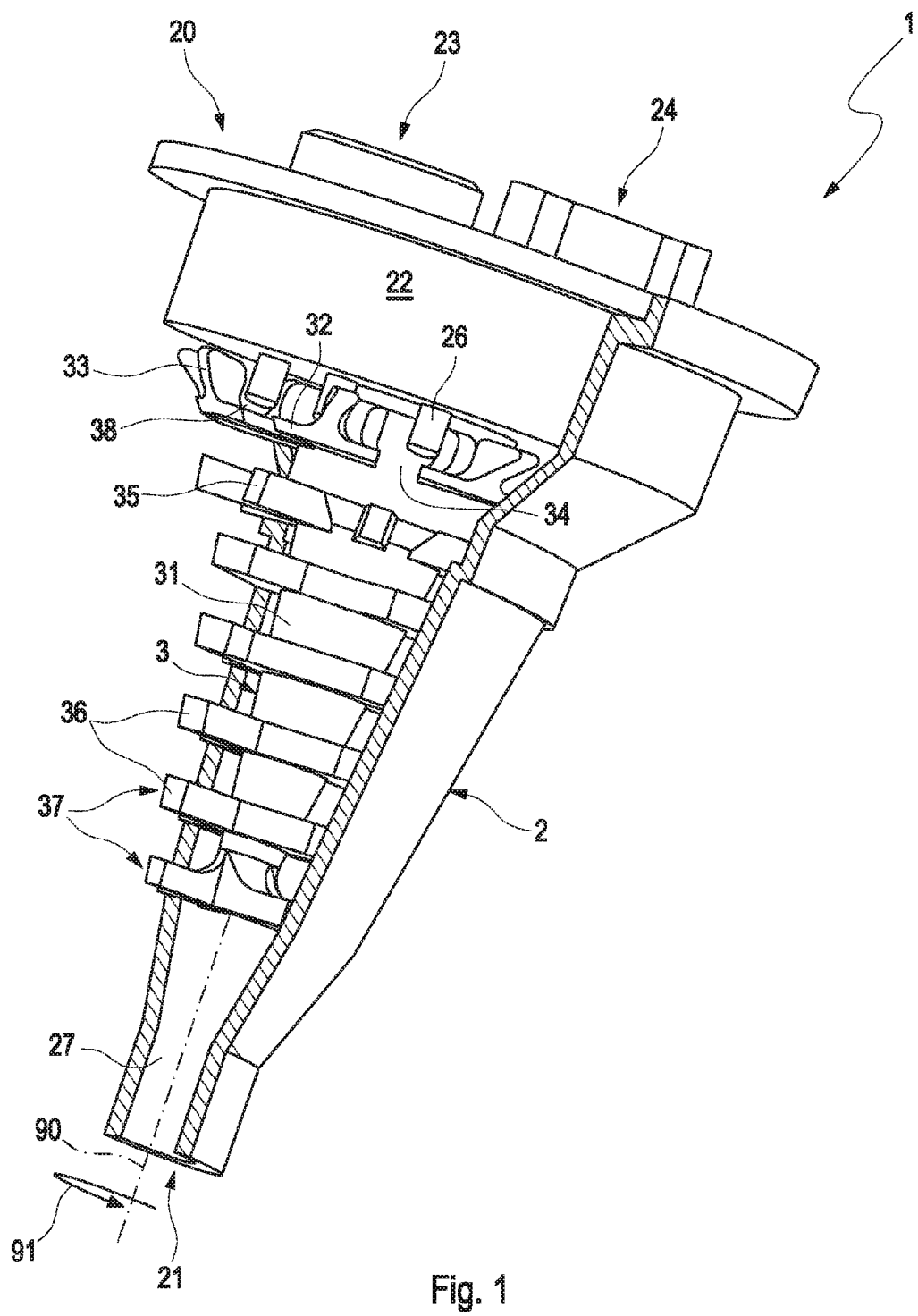
FIG. 1 shows a first embodiment of a dynamic mixer according to the invention.

In FIG. 1, a dynamic mixer 1 according to the invention is illustrated, wherein the mixing tube 2 is illustrated only in part in order to show the interior of the dynamic mixer.

The mixer 1 includes a mixing tube 2 and a rotor 3 that is arranged therein and is mounted to be rotatable about the axis 90. The rotor 3 has a preferred predetermined direction of rotation, which is indicated by the arrow 91.

Figure 2:
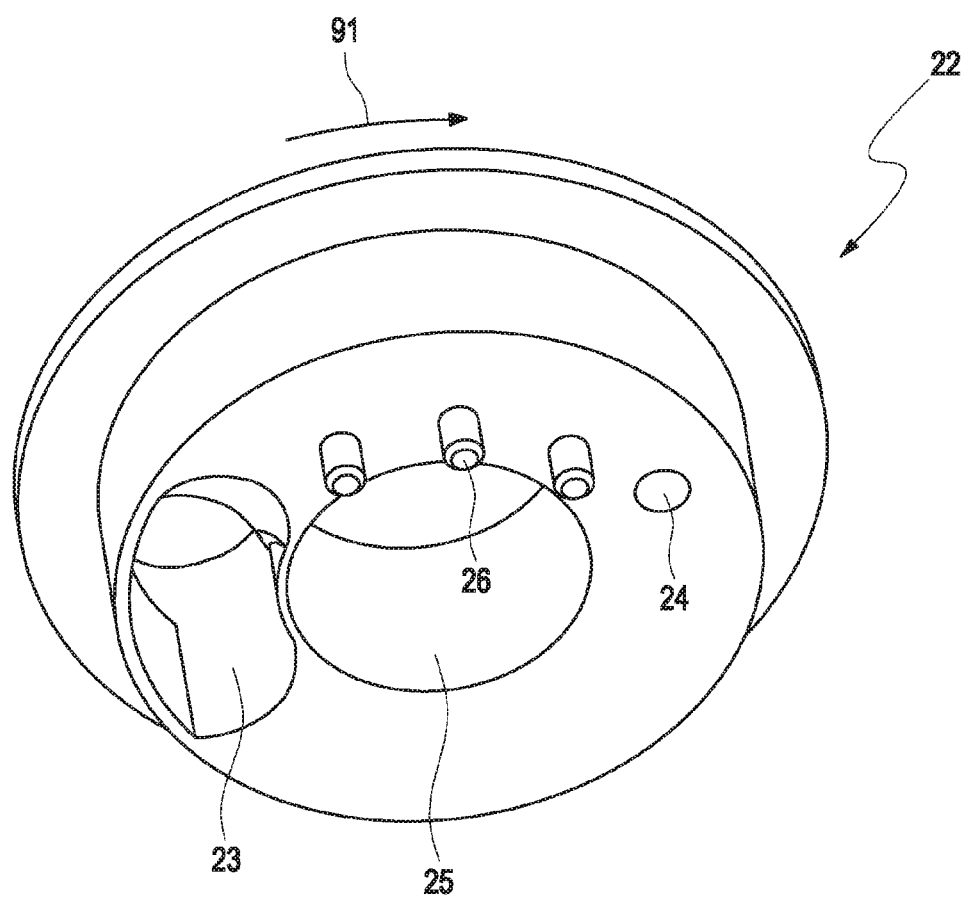
FIG. 2 shows a detail illustration of the end wall of the dynamic mixer from FIG. 1.

The mixing tube 2 is constructed at its first end 20 for connection to a discharge arrangement (for example MixStar, DMG; Pentamix, 3M) that includes a container having discharge openings and a discharge device (not illustrated) for the two components of a dental impression compound, and at its other end has an outlet opening 21. At the first end 20 there is provided an end wall 22 that has a first and a second inlet opening 23, 24 (cf. FIG. 2). Here, the first inlet opening 23 is constructed as the inlet opening for the base paste of a dental impression compound, while the second inlet opening 24 is constructed for the catalyst paste of the impression compound. Since the mixing ratio in the illustrated mixer 1 is approximately 5:1, the first inlet opening 23 is markedly larger than the second inlet opening 24. Similarly, an opening 25 is provided in the end wall 22 for the rotor 3 to pass through.

Figure 3:
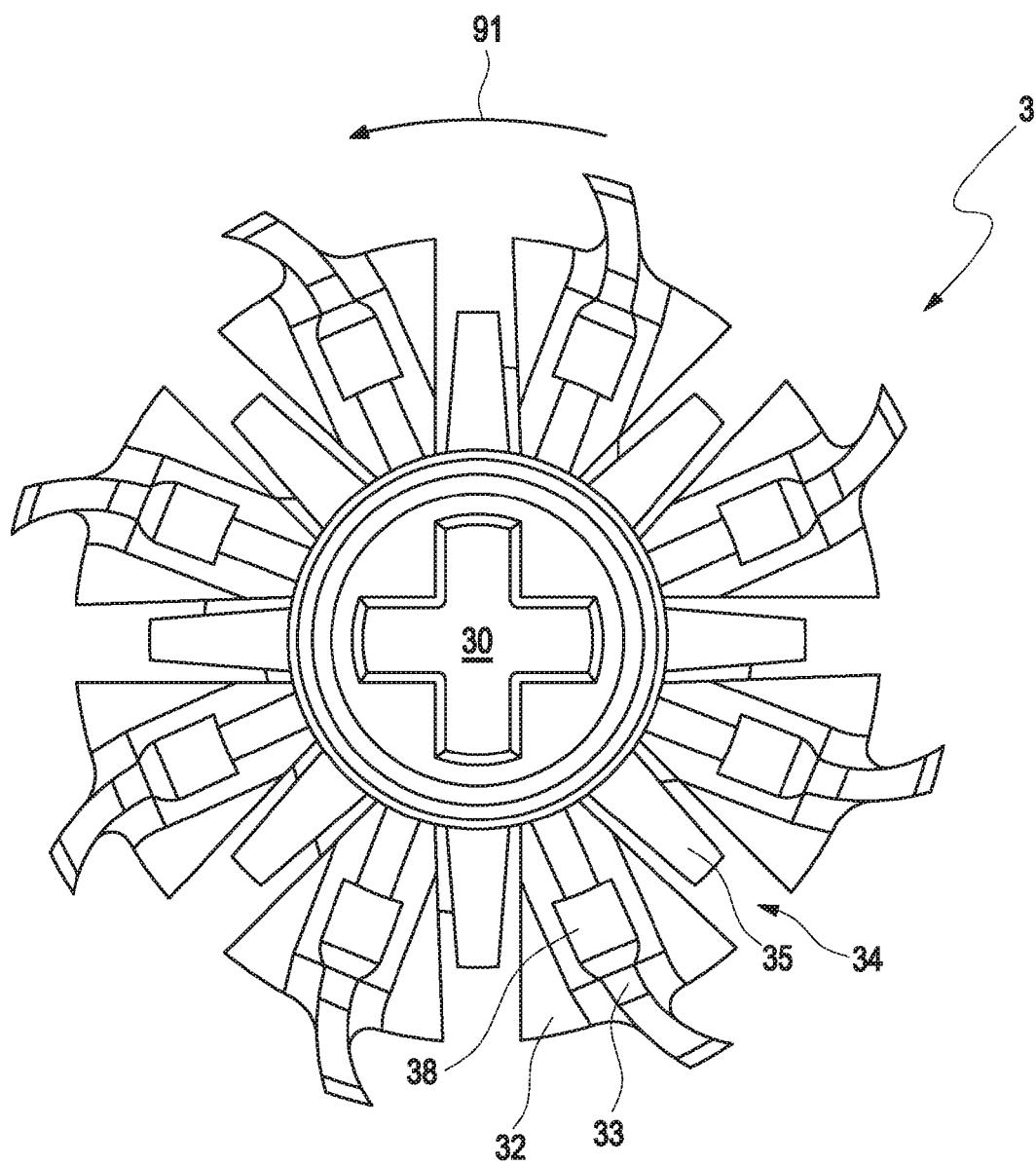
FIG. 3 shows a plan view of the rotor of the dynamic mixer from FIG. 1.

The rotor 3 can be coupled to a drive element (not illustrated) by way of a coupling 30 that is located at the first end 20 of the mixing tube 2 (cf. FIG. 3). For this purpose, the rotor 3 is guided through the opening 25 and is also mounted in this opening 25. The drive element can in particular be part of the discharge device and drive the rotor 3 in the predetermined direction of rotation 91.

The rotor 3 has a rotor disk 32 that is arranged on the rotor hub 31 and has entraining elements 33 that are directed toward the end wall 22, wherein the outer ends of the individual entraining elements 33 are curved around in the direction of rotation 91 of the rotor 3, in the form of buckets. Rotor disk openings 34 that are in the form of a gap in the radial direction are provided between the individual entraining elements 33. On the side of the rotor disk 32 that is remote from the end wall 22, arms 35 that are substantially flush with the rotor disk openings 34 are provided on the rotor hub 31.

Provided on the rotor hub 31 further toward the outlet opening 21 of the mixing tube 2 are mixing elements 36, wherein the mixing elements 36 are arranged in five mixing element groups 37, in which all the associated mixing elements 36 are arranged in a plane perpendicular to the axis 90 of the rotor 3. The mixing elements 36—as indeed the entraining elements 33 and the arms 35—each extend from the rotor hub 31 of the rotor 3 as far as the inner wall 27 of the mixing tube 2.

Provided on the end wall 22, between the first and the second inlet openings 23, 24 as seen in the direction of rotation 91 of the rotor 3, are three pins 26, which project in the direction of the rotor disk 32. The region further in the direction of rotation of the rotor 3, between the second and the first inlet openings 24, 23, is free of pins. Here, the pins 26 are all arranged at the same spacing from the axis 90 of the rotor 3. The entraining elements 33 on the rotor 3 have recesses 38 through which the pins 26 that project from the end wall 22 can slide as the rotor 3 rotates. Consequently, the pins 26 do not therefore impede rotation of the rotor 3 about its axis 90.

The mode of operation of the illustrated dynamic mixer 1 will now be presented with reference to an exemplary use. In this example, the mixer 1 is used for the preparatory mixing of a dental impression compound that comprises two components—a base paste and a catalyst paste. Here, the two components are intended to be mixed in a ratio of 5:1, wherein the base paste usually has a markedly higher viscosity than the catalyst paste.

The dynamic mixer 1 is connected at the first end 20 of the mixing tube 2 to discharge openings and a discharge device for the two components of a dental impression compound. Use is such that the discharge device presses the first component—the base paste—through the first inlet opening 23 and the second component—the catalyst paste—through the second inlet opening 24 and into the mixer 1. At the same time, a drive unit of the discharge device is connected by way of the coupling 30 to the rotor 3 of the mixer 1 such that the drive unit can drive the rotor 3 in the predetermined direction of rotation 91.

The discharge device introduces the base paste through the first, larger inlet opening 23 and into the mixer 1. There it is entrained by the entraining elements 33 of the rotor, which is driven by the drive unit of the discharge device, and is conveyed past the pins 26 in the direction toward the second, smaller inlet opening 24. As a result of the pins 26, which can slide through the recesses 38 in the entraining elements 33, the base paste is subjected to shear force, as a result of which its viscosity is reduced.

The catalyst paste is added through the second inlet opening 24, and this is blended more effectively with the base paste because of the reduction in viscosity of the latter. The mixture of base paste and catalyst paste, which at this point in time is still relatively heterogeneous, then passes through the rotor disk openings 34, past the arms 35, and reaches the mixing elements 36. The base paste and catalyst paste continue to be blended with one another by the mixing elements 36, which are arranged in mixing element groups 37, such that a homogeneous mixture is output from the outlet opening 21, at the end of the mixing tube 2. The output mixture is in this case homogenized to such an extent that it is directly usable as a dental impression compound.

As a result of the mixer according to the invention, neither the temperature nor the ejection pressure of the components or the mixture is appreciably increased even by comparison with other dynamic mixers that are known from the prior art, while homogenization is excellent, with the result that the predetermined processing times and hardening times of the impression compounds are guaranteed.

Figure 4:
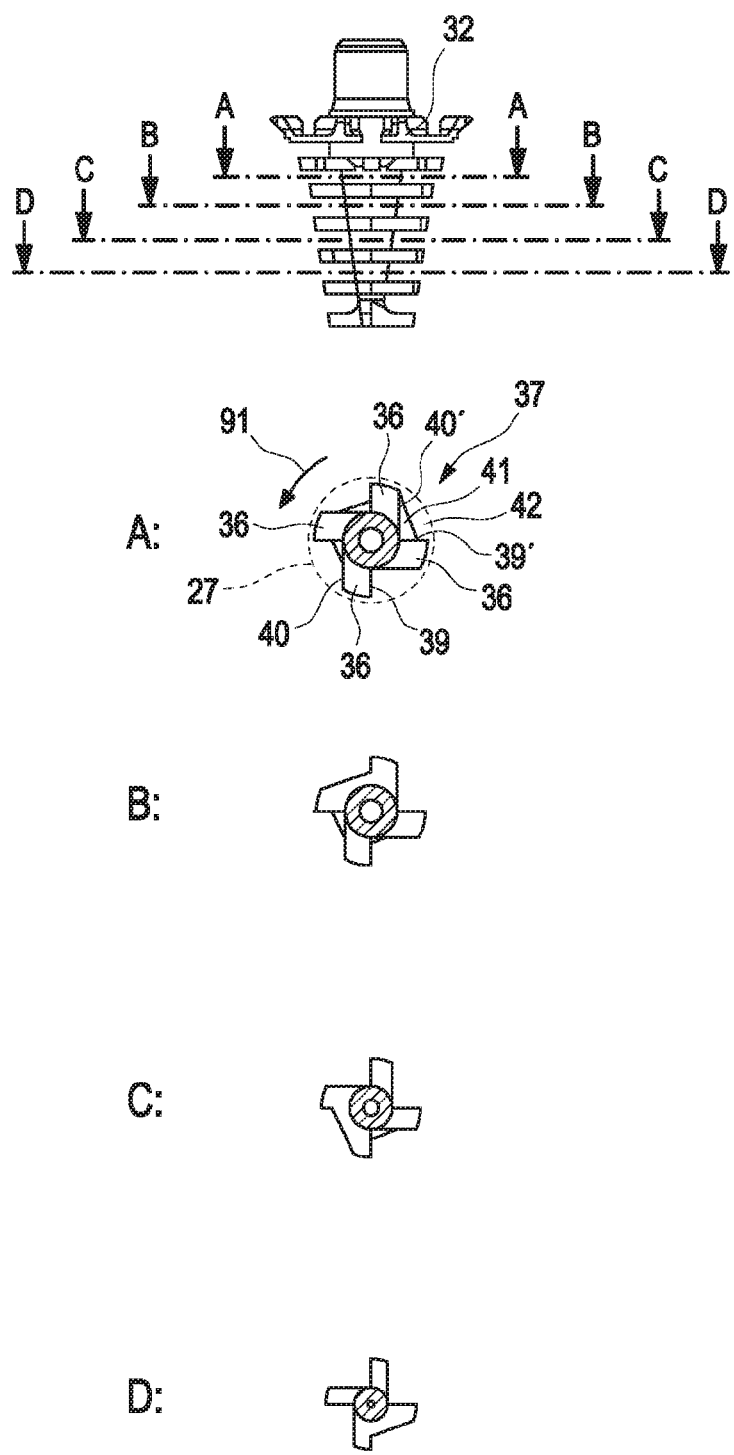
FIG. 4 shows a side view and four sectional views of the rotor of the dynamic mixer from FIG. 1.

In FIG. 4, further details of the rotor 3 are illustrated, wherein in addition to a side view of the rotor 3 the figure also includes four sectional illustrations A-D. In the sectional illustrations A-D, in each case the mixing elements 36 of the first four mixing element groups 37, as seen from the rotor disk 32, are shown.

Each mixing element group 37 includes four mixing elements 36, which are arranged uniformly distributed over the periphery of the rotor hub 31. In the mixing elements 36, the front edge 39, as seen in the direction of rotation 91, is parallel to the rear edge 40. Furthermore, the mixing elements 36 each extend as far as the inner wall 27 of the mixing tube 2, which in FIG. 4A is illustrated by way of example by a dotted line.

In the mixing element group 37 that are shown in the sectional illustrations in FIG. 4, a deflecting element 41 is provided in each case between two mixing elements 36. Here, the deflecting element 41 is arranged between the front edge 39' of a first mixing element 36 and the rear edge 40' of the adjacent mixing element 36. As a result of the deflecting element 41, the free surface between these two mixing elements 36 is made smaller.

It goes without saying that the deflecting element 41 need not be arranged between two mixing elements 36. It is also possible for the deflecting element 41 to be constructed in a manner detached from the mixing elements 36.

The fifth and last mixing element group 37, as seen from the from the rotor disk 32, does not include a deflecting element 41.

The invention claimed is:

1. A dynamic mixer for the components of viscous compounds, the mixer having a mixing tube and, arranged therein, a drivable rotor rotatable around an axis, wherein the mixing tube has at a first end an end wall having at least two inlet openings for the components, and at a second end an outlet opening for a mixture,
    wherein the rotor has a rotor disk having at least one entraining element that faces the end wall, and at least one rotor disk opening for components to pass through to a side of the rotor disk remote from the end wall, wherein at least one mixing element is arranged on a rotor hub between the rotor disk and the outlet opening of the mixing tube,
    the mixing tube characterized in that at least one projecting pin is arranged on the end wall toward the rotor disk, and the at least one entraining element has at least one recess for the at least one pin, wherein the at least one pin is arranged, as seen in the direction of rotation of the rotor, between a first, larger inlet opening and a second, smaller inlet opening.

2. The mixer as claimed in claim 1, characterized in that the at least one pin has a length that is at least ⅔ of the spacing from the end wall to the rotor disk, or the at least one pin extends as far as the rotor disk.

3. The mixer as claimed in claim 1, characterized in that the height of the at least one entraining element of the rotor disk and the length of the at least one pin are substantially the same.

4. The mixer as claimed in claim 1, characterized in that the spacing between the end wall and the rotor disk is at least 5% of the total length of the mixing tube.

5. The mixer as claimed in claim 4, characterized in that the spacing between the end wall and the rotor disk is at least 10% of the total length of the mixing tube.

6. The mixer as claimed in claim 4, characterized in that the spacing between the end wall and the rotor disk is 10 to 30% of the total length of the mixing tube.

7. The mixer as claimed in claim 1, characterized in that more than one pin is provided on the end wall, wherein the pins or at least groups of pins are arranged in each case at the same spacing from the axis of the rotor.

8. The mixer as claimed in claim 1, characterized in that the end of the at least one entraining element that is remote from the axis of the rotor is curved around in the direction of rotation.

9. The mixer as claimed in claim 1, characterized in that the at least one rotor disk opening is a radial slot.

10. The mixer as claimed in claim 9, wherein, on the side of the rotor disk remote from the end wall, at least one arm that is flush with the at least one slot is arranged on the rotor hub.

11. The mixer as claimed in claim 1, characterized in that at least one mixing element comprises more than one mixing element.

12. The mixer as claimed in claim 11, characterized in that a deflecting element is provided in a mixing element group.

13. The mixer as claimed in claim 12, wherein the deflecting element is a connecting surface between two adjacent mixing elements and the free surface between these two mixing elements is made smaller.

14. The mixer as claimed in claim 11, wherein mixing elements are arranged in a plurality of mixing element groups that are spaced in the axial direction of the axis of the rotor, wherein the mixing elements of a mixing element group are arranged in a plane perpendicular to the axis of the rotor.

* * * * *